United States Patent [19]

Derrien et al.

[11] 4,185,089
[45] Jan. 22, 1980

[54] IMMUNOLOGICAL ADJUVANT CONSTITUTED BY THE P-AMINO-PHENYL DERIVATIVE OF N-ACETYL-MURAMYL-L-ALANYL-D-ISO-GLUTAMINE

[75] Inventors: Marcel Derrien, Rambouillet; Edgar Lederer, Sceaux; Francoise M. Audibert, Neuilly-sur-Seine; Louis Chedid; Jean Choay, both of Paris; Pierre Lefrancier, Bures-sur-Yvette, all of France

[73] Assignee: Agence Nationale de Valorisation de la Recherche (ANVAR), Neuilly-sur-Seine, France

[21] Appl. No.: 845,105

[22] Filed: Oct. 25, 1977

[30] Foreign Application Priority Data

Oct. 22, 1976 [FR] France ............... 76 31935

[51] Int. Cl.$^2$ ............... A61K 39/00; A61K 37/48; A61K 37/02; C07C 103/52
[52] U.S. Cl. ............... 424/88; 424/93; 424/177; 260/112.5 R
[58] Field of Search ............... 424/177, 88, 93; 260/112.5 R

[56] References Cited

U.S. PATENT DOCUMENTS

| | | | |
|---|---|---|---|
| 4,082,735 | 4/1978 | Jones et al. | 424/177 |
| 4,082,736 | 4/1978 | Jones et al. | 424/177 |

OTHER PUBLICATIONS

F. Ellouz, et al., Biochem. and Biophysical Res. Communication 59, 1974, pp. 1317–1325.

Ghuysen et al., Bact. Membranes and Walls, 1973, pp. 39–41.
Chaturvedi, J. Med. Chem. 9, 1966, pp. 971–973.
Kotani et al., Sympos. Internat. or Bact. Immun. Stimulants, 1973, p. 8.
Lamzelotti et al., J. Am. Chem. Soc. 86, 1964, pp. 1880–1881.
Kotani et al., Biken J. 13, 105–111, 1975.
Adam et al., Biochem. and Biophys. Res. Comm. 72, 1976, pp. 339–346.
Chem. Abst. 87, 1977, pp. 199018m, 118075c, 51519e.

*Primary Examiner*—Delbert R. Phillips
*Attorney, Agent, or Firm*—Weiser, Stapler & Spivak

[57] ABSTRACT

The adjuvant is 2-(p-amino-phenyl-2-acetamido-2-deoxy-3-O-D-glucopyranosyl)-D-propionyl-L-alanyl-D-isoglutamine, which compound in its $\beta$ glucoside form, corresponds with the formula

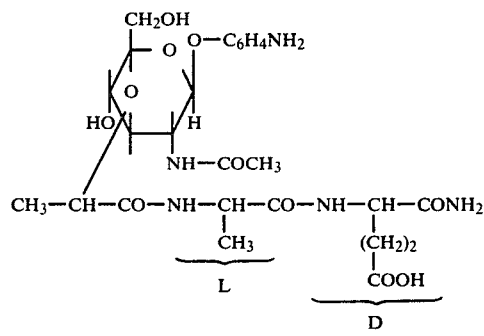

It is notably useful for favoring immunitory responses relative to antigens of low immunogenicity.

14 Claims, No Drawings

IMMUNOLOGICAL ADJUVANT CONSTITUTED BY THE P-AMINO-PHENYL DERIVATIVE OF N-ACETYL-MURAMYL-L-ALANYL-D-ISOGLUTAMINE

BACKGROUND OF THE INVENTION

The invention relates to a novel water soluble agent, effective as an immunological adjuvant to stimulate immunitary responses in a host.

The invention also relates to the process for the preparation of this agent as well to medicinal compositions including it.

GENERAL DESCRIPTION OF THE INVENTION

The adjuvant agent according to the invention is 2-(p-amino-phenyl-2-acetamido-2-deoxy-3-O-D-glucopyranosyl)-D-propionyl-L-alanyl-D-isoglutamine, and more particularly its β glucoside form corresponding to the formula

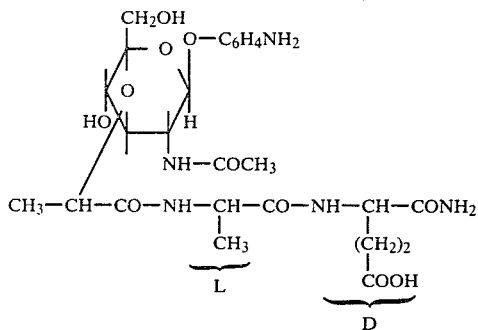

This will be denoted below by the abbreviation p-amino phenyl-Mur-NAc-L-Ala-D-iso-Gln.

According to another aspect of the invention, a process for preparing compound (A) comprises, in the first stage, synthesis of the fragment corresponding to the peptide chain L-Ala-D-iso-Gln, and that of fragment denoted by the abbreviation p-amino-phenyl-Mur-NAc, the functional groups which must not react being previously protected, and then in a second stage, coupling these two fragments. Finally the catalytic reduction of the nitro group into an amino group is carried out at the same time as all the protecting groups are hydrolysed.

It is also possible to carry out the synthesis of the compound (A) by effecting separate coupling of a derivative of p-amino-phenyl-Mur-NAc with a derivative of L-alanine, then coupling the resulting product with an adequate derivative of D-isoglutamine, according to the traditionally used processes in peptide synthesises.

The invention also relates to medicinal compositions containing said agent and serving notably to re-inforce the action of weak immunogens. More particularly, the invention relates to compositions containing said agent and useful for immunisation of man and of warm-blooded animals against bacterial, viral and parasitic diseases, and against different tissular antigens of normal or pathological origin.

The product according to the invention can be administered in various ways, but preferably, it is injected or administered by local scarification. For this purpose, it is advantageous to use medicinal compositions constituted by emulsions of effective doses of the product according to the invention in a pharmaceutically acceptable medium. In particular, media containing an oily phase, and notably water in oil emulsions are used. To form these emulsions, it is possible to use paraffin oils or similar oils, preferably, metabolisable vegetable oils are selected such as those described in French patent application No. 75 04003, or any other composition based on a vegetable oil enabling the production of equivalent results.

The product according to the invention has the particularity, when it is administered, of not being pyrogenic. This property, which distinguishes it from certain previously known compounds, permits in particular administration by the intravenous route without risk of hyperthermic shock to the patient.

To permit extemporaneous preparation of the medicinal compositions and notably of the emulsions, the adjuvant agent can also be in lyophilised form.

An avantageous pharmaceutical form comprises unit doses of about 25 to 100 mg of the adjuvant product according to the invention, preferably of about 50 mg.

The invention relates also to medicinal compositions in which p-amino-phenyl-Mur-NAc-L-Ala-D-iso-Gln is associated with an immunogenic agent, notably with a weak vaccinating antigen.

In addition to its use as an adjuvant in vaccine compositions, compound (A) is useful as a laboratory reactant. It is for example, applicable either as an amplifier of immunitary responses, more particularly when the immunogenicity of the antigens is weak, or as an antagonist of the possible immunosuppressive action of the products tested as immunosuppressors in currently studied biological tests.

DESCRIPTION OF PREFERRED EMBODIMENTS

Other features of the invention will appear in the course of the description of an example of the preparation of the product according to the invention, as well as of the tests establishing the pharmacological properties of this product.

(1) EXAMPLE OF THE SYNTHESIS OF 2-(P-AMINO-PHENYL-2-ACETAMIDO-2-DEOXY-3-O-β-D-GLUCOPYRANOSYL)-D-PROPIONYL-L-ALANYL-D-ISOGLUTAMINE (a) p-nitrophenyl-2-acetamido-4,6-O-benzylidene-3-O-(D-1-carboxyethyl)-2-deoxy-β-D-glucopyranoside (I)

To 1.72 g (4 m moles) of p-nitrophenyl-2-acetamido-4,6-O-benzylidene-2-deoxy-β-D-glucopyranoside obtained by the method described by Jeanloz R. W., Walker E. and Sinay P. in Carbohydr. Res. (1968), 6, 184, in solution in 1 liter of anhydrous dioxane, is added, at 68° C., 1.36 g (28 m moles) of a 50% suspension of sodium hydride in oil. After stirring for 15 minutes, 6.8 ml (90 m moles) of chloropropionic acid were added. The reaction mixture was stirred for 2 hours at 68° C. After a further addition of the sodium hydride suspension (18 g, 375 m moles) and stirring for 10 minutes, the reaction mixture was brought to 50° C., with stirring, for about 14 hours.

The excess sodium hydride was destroyed, at 0° C., by the addition of 100 ml of water. Two phases form. The upper phase is separated, filtered and concentrated. The residue obtained was dissolved in 200 ml of water. This aqueous phase was extracted by four lots of 100 ml of chloroform, then filtered and acidified by 2.5 N HCl (pH 3), at 0° C. A precipitate was formed which was extracted by 500 ml of chloroform. After drying over magnesium sulfate, the chloroform was evaporated. The residue obtained was dissolved in 50 ml of hot methanol and the product was precipitated by the addition of water. In this manner 1 g of the product sought was obtained, namely a yield of 50%. Its melting point was M.P. 220°–222° C. and its rotatory power $[\alpha]_D^{25} = +8°$ (dimethylformamide). Elementary analysis of this product is as follows:

| $C_{24} H_{26} O_{10} N_2$ (502.48) | C | H | N |
|---|---|---|---|
| calculated: | 57.37 | 5.22 | 5.57 |
| found | 57.01 | 6.02 | 5.0 |

(b) Benzyl ester of 2-(p-nitrophenyl-2-acetamido-4,6-O-benzylidene-2-deoxy-3-O-β-D-glucopyranosyl)-D-propionyl-L-alanyl-D-isoglutamine (II)

408 mg (1 m mole) of the benzyl ester of BOC*-L-alanyl-D-isoglutamine, obtained by the method described by Lefrancier P. and Bricas E. in Bull. Soc. Chim. Biol. (1967), 49, 1257, were treated by 3 ml of a normal solution of hydrochloric acid in glacial acetic acid. After 30 minutes, the reaction mixture was concentrated to dryness and dried.
*BOC=ter.butyloxycarbonyl The oil obtained was taken up in 10 ml of dimethylformamide containing 0.11 ml (1 m mole) of N-methylmorpholine. There was then added, at −15° C., a solution, previously prepared at this same temperature, of 502 mg (1 m mole) of (I), of 0.11 ml (1 m mole) of N-methylmorpholine and of 0.13 ml (1 m mole) of isobutylchloroformate.

The reaction mixture was stirred for four hours at −15° C., then 1.7 ml of a 2.5 M solution of $KHCO_3$ were added at 0° C. After 30 minutes, the product was precipitated by the addition of distilled water, then filtered, washed with water and dried. There was thus obtained 554 mg, namely a yield of 87% of the desired product which is homogeneous and can be used without further purification.

(c) 2-(p-amino-phenyl-2-acetamido-2-deoxy-3-O-β-D-glucopyranosyl)-D-propionyl-L-alanyl-D-isoglutamine (III)

550 mg (0.7 m moles) of (II), in solution in 150 ml of glacial acetic acid were hydrogenated, for 46 hours, in the presence of 550 mg of 5% palladium on carbon. After filtration of the catalyst and concentration to dryness, the product was precipitated from the methanol-acetone-ether mixture. 350 mg of product were obtained, namely a yield of 86%.

A fraction of 180 mg of the product was chromatographed on a column (22×1.7 cm), charged with an ion exchange resin marketed under the name AG1X 2 by the BIORAD Company, in its acetate form, and equilibrated with a 0.002 N acetic acid solution. The product was eluted with a 0.02 N acetic acid solution. The interesting fractions were combined, concentrated and the product was re-precipitated, as previously, from a methanol-acetone-ether mixture. 98 mg are obtained, namely 55% yield of the desired final product whose rotatory power was $[\alpha]_D^{25} = +32.7°$ (absolute methanol). The elementary analysis of the product gave the following results:

| $C_{25} H_{37} O_{11} N_5$ (583.62) | C | H | N |
|---|---|---|---|
| calculated: | 51.45 | 6.39 | 12.00 |
| found: | 51.51 | 6.54 | 11.52 |

(2) PHARMACOLOGICAL PROPERTIES

Adjuvant character in the presence of an oily phase

In these tests, the growth of the specific antibody level of a given antigen when the latter is injected, with or without the adjuvant compound according to the invention, in the midst of a water and oil emulsion was followed.

The tests were carried out on female Hartley guinea pigs of 350 g. The administration was done by intradermal injection in the plantar pad of each of the rear paws. The ovalbumin (constituting the antigen) in the dose of 0.5 mg was prepared in 0.1 ml of an emulsion of saline isotonic solution, in an oily phase constituted either by the Freund incomplete adjuvant (FIA), or by the Freund complete adjuvant (FCA) formed by the FIA to which is added 0.1 mg of whole cells of *Mycobacterium smegmatis*. The compound according to the invention was administered in the dose of 0.1 mg added in the emulsion containing the FIA.

Eighteen days after this immunisation, possible reactions of delayed hypersensibility to the antigen were sought by injecting by the intradermal route 0.005 mg of ovalbumin into the side of the animals, and the reaction at the point of injection was observed 48 hours later. The diameter in mm of the thus provoked reaction was measured.

Twenty one days after the injection, the animals were bled. On the serum collected, the specific antibody content of the ovalbumin was measured by precipitation of the antibody-antigen complex in the equivalence zone. The amount of protein nitrogen contained in this precipitate was evaluated according to the Folin method. The average values of the content of antibodies are indicated in the table of results. These values express the amounts, in micrograms, of nitrogen precipitable by the antigen, per ml of serum.

The results of these tests are reported in the following table.

| Composition of the emulsion containing the antigen | Seric antibodies(μg/ml) | Cutaneous test diameter in mm |
|---|---|---|
| FIA | < 500 | 0 |
| FCA (100 μg) | 2000 | 9±2.7 |
| FIA+p-amino-phenyl-Mur-NAc-L-Ala-D-iso-Gln (100 μg) | 3500 | 19.5±4.5 |

These results show that p-amino-phenyl-Mur-NAc-L-Ala-D-iso-Gln, administered in oily emulsion, distinctly facilitates the increase in the level of antibodies to the administered antigen, and that it induces a hypersensitivity reaction of the delayed type with respect to the same antigen.

Toxicity

The toxicity of the product according to the invention was studied by intravenous injection in mice aged two months. By gradually increasing the administered doses, it was shown that the lethal dose ($LD_{50}$), that is to say that the dose for which the mortality of the animals, following the injection, is 50%, is of an order of magnitude very much higher than that of the dosage at which the product manifests its adjuvant properties.

Pyrogenicity

The pyrogenic effect of the product according to the invention on rabbits was studied, following the protocol of the French Pharmacopea, 9e edition, II-235.

Each test was carried out on a batch of three rabbits. The administration was first done by the subcutaneous route, then by the intravenous route. The results of these tests, that is to say the increase in temperature in the treated animals, were as follows:

| Administration | Dose | Rise in temperature °C. | | |
| --- | --- | --- | --- | --- |
| Sub-cutaneous | 0.500 mg/kg | 0 | 0.2 | 0.1 |
| sub-cutaneous | 0.100 mg/kg | 0 | 0 | 0.1 |
| intraveneous | 1.0 mg/kg | 0 | 0.4 | 0.6 |

The product according to the invention was hence apyrogenic at doses where its adjuvant properties are manifested.

Hence apyrogenic adjuvant compositions are obtained devoid of toxicity and which can be used to increase the effectiveness of vaccines of bacterial or viral origin, notably when the latter are weakly immunogenic.

They can be used notably to facilitate the immunisation of the host (human or animal patients) with respect to infection of bacterial or viral origin, of antigens of tumors, etc. They are also effective for the manufacture of serums containing antibodies active with respect to these antigens.

We claim:

1. 2-(p-amino-phenyl-2-acetamido-2-deoxy-3-O-D-gluco-pyranosyl)-D-propionyl-L-alanyl-D-isoglutamine, which compound, in its β glucoside form, corresponds to the formula

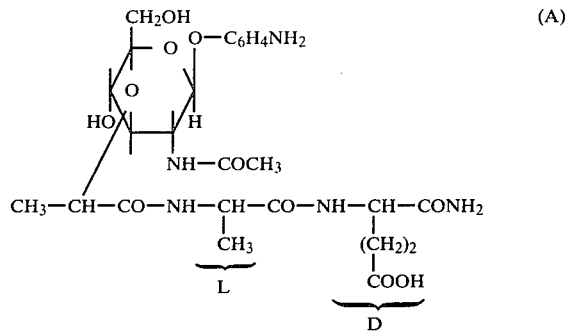

2. A biological composition which comprises a pharmaceutically acceptable carrier and an effective amount of the compound 2-(p-amino-phenyl-2-acetamido-2-deoxy-3-O-D-gluco-pyranosyl)-D-propionyl-L-alanyl-D-isoglutamine.

3. The composition according to claim 2, which is an injectable emulsion containing an effective dose of the compound.

4. The composition according to claim 3, which is a water and oil emulsion.

5. The composition according to claim 3, wherein the oil is constituted by a metabolisable oil.

6. The composition according to claim 2, wherein the compound therein is associated with an immunogenic agent.

7. Vaccine composition for human use containing an immunogenic agent and an effective dose of the compound 2-(p-amino-phenyl-2-acetamido-2-deoxy-3-O-D-gluco-pyranosyl)-D-propionyl-L-alanyl-D-isoglutamine.

8. Vaccine composition for veterinary use containing an immunogenic agent and an effective dose of the compound 2-(p-amino-phenyl-2-acetamido-2-deoxy-3-O-D-gluco-pyranosyl)-D-propionyl-L-alanyl-D-isoglutamine.

9. A method of treating diseases in humans or animals by administrering as an immunological adjuvant, an effective amount of the compound 2-(p-amino-phenyl-2-acetamido-2-deoxy-3-O-D-gluco-pyranosyl)-D-propionyl-L-alanyl-D-isoglutamine.

10. The composition of claim 2 which comprises also an immunogen.

11. The composition of claim 2 which has no pyrogenicity at dosage where the compound is adjuvant.

12. The composition of claim 10 wherein the immunogen is a weak immunogen.

13. The composition of claim 2 wherein the compound is in unit dosage of about 25 to 100 mg.

14. The method of claim 9 which comprises causing an immunogenic reaction but no pyrogenicity.

* * * * *